(12) United States Patent
Yoneyama

(10) Patent No.: US 7,778,389 B2
(45) Date of Patent: Aug. 17, 2010

(54) X-RAY IMAGING SYSTEM AND METHOD

(75) Inventor: Akio Yoneyama, Kawagoe (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 12/213,735

(22) Filed: Jun. 24, 2008

(65) Prior Publication Data
US 2009/0003517 A1    Jan. 1, 2009

(30) Foreign Application Priority Data
Jun. 26, 2007    (JP)    ............... 2007-168095

(51) Int. Cl.
*G01N 23/207* (2006.01)
*G01N 23/201* (2006.01)
*G03H 5/00* (2006.01)
*G21K 1/06* (2006.01)

(52) U.S. Cl. ............... 378/70; 378/36; 378/85; 378/87

(58) Field of Classification Search ............ 378/70–81, 378/86, 87, 210; 250/370.01, 370.08, 370.09, 250/390.1, 503.1; 356/128, 131, 132, 237.1; 359/211.6, 223.1, 224.1, 226.1, 226.2, 362–366, 359/558, 563, 577–579, 618, 629, 639, 726, 359/730, 733–736, 801, 809, 811, 839
See application file for complete search history.

(56) References Cited

U.S. PATENT DOCUMENTS

| | | | | |
|---|---|---|---|---|
| 3,407,296 A | * | 10/1968 | Armstrong | 378/36 |
| 3,446,961 A | * | 5/1969 | Ulrich et al. | 378/36 |
| 5,259,013 A | | 11/1993 | Kuriyama | |
| 5,579,363 A | * | 11/1996 | Ingal et al. | 378/84 |
| 5,850,425 A | | 12/1998 | Wilkins | |
| 5,930,325 A | * | 7/1999 | Momose | 378/36 |
| 6,804,324 B2 | * | 10/2004 | Martynov et al. | 378/36 |
| 7,154,992 B2 | * | 12/2006 | Schuster | 378/79 |
| 7,280,634 B2 | * | 10/2007 | Verman et al. | 378/85 |
| 7,286,628 B2 | * | 10/2007 | Donnelly et al. | 378/4 |

(Continued)

FOREIGN PATENT DOCUMENTS

EP    1 722 216    11/2006

(Continued)

OTHER PUBLICATIONS

U. Bonse et al., "An X-ray Interferometer", Appl. Phys. Lett. 6, 155 (1965).

(Continued)

*Primary Examiner*—Edward J Glick
*Assistant Examiner*—Anastasia Midkiff
(74) *Attorney, Agent, or Firm*—Antonelli, Terry, Stout & Kraus, LLP.

(57) ABSTRACT

The present invention provides an X-ray imaging system and method capable of performing time-resolved observation in a short measurement time at the same density resolution and in the same dynamic range as those for a diffraction enhanced X-ray imaging method, and also capable of observing a sample with high sensitivity even if the intensity of an incident X-ray varies with time. A refraction angle of X-ray beams caused by the sample is detected at a time by X-ray imagers by utilizing multiple X-ray diffractions by multiple analyzer crystals.

20 Claims, 12 Drawing Sheets

U.S. PATENT DOCUMENTS

| | | | |
|---|---|---|---|
| 2001/0038680 A1* | 11/2001 | Davidson | 378/43 |
| 2002/0027970 A1* | 3/2002 | Chapman et al. | 378/62 |
| 2005/0117699 A1* | 6/2005 | Yoneyama | 378/36 |
| 2006/0256918 A1* | 11/2006 | Yoneyama et al. | 378/82 |
| 2008/0019482 A1 | 1/2008 | Yoneyama et al. | |

FOREIGN PATENT DOCUMENTS

| | | |
|---|---|---|
| JP | 04-348262 | 12/1992 |
| JP | 5-340894 | 12/1993 |
| JP | 09-187455 | 7/1997 |
| JP | 2008-026098 | 2/2008 |

OTHER PUBLICATIONS

P. Becker et al., "The Skew-Symetric Two-Crystal X-ray Interferometer", J. Appl. Cryst. 7, 593 (1974).

J.H. Bruning et al., "Digital Wavefront Measuring Interferometer for Testing Optical Surfaces and Lenses", Appl. Opt. 13 (1974), pp. 2693.

M. Ando et al., "A New Optics for Dark-Field Imaging in X-ray Region 'Owl'", Jpn. J. Appl. Phys. 40 (2001) pp. L844.

D. Chapman et al., "Diffraction Enhanced X-ray Imaging", Phys. Med. Biol. 42 (1997) pp. 2015.

Kobayashi et al "X-ray phase contrast imaging study of activated carbon/carbon composite", Jan. 1, 2000, Materials Research Society Symposium Proceedings, Materials Research Society, Pittsburg, PA pp. 273-278.

* cited by examiner $\theta_A = -0.5$ sec        $\theta_A = 0$ sec        $\theta_A = +0.5$ sec Intensity changes at each sample position

A        B        C

X-RAY IMAGING SYSTEM AND METHOD

CLAIM OF PRIORITY

The present application claims priority from Japanese application JP 2007-168095 filed on Jun. 26, 2007, the content of which is hereby incorporated by reference into this application.

BACKGROUND OF THE INVENTION

1. Field of the Invention

The present invention relates to an X-ray imaging system and method for nondestructive testing of the inside of an object.

2. Description of the Related Art

Imaging systems for nondestructive observation of the inside of a sample using X-rays include an absorption-contrast X-ray imaging system using a change in X-ray intensity caused by the sample as image contrast, and a phase-contrast X-ray imaging system using a change in phase as the contrast. The former, namely, the absorption-contrast X-ray imaging system, is mainly composed of an X-ray source, a sample setting mechanism and a detector. The X-rays emitted from the X-ray source are irradiated on the sample positioned by the sample placement mechanism, and the X-rays that have passed through the sample are detected by the detector. Thereby, an image using the change in the intensity of X-rays caused by the sample absorption as the contrast is obtained. Because of a simple principle of measurement and a simple system configuration, this system is widely used in many fields including medical diagnosis, in the name of roentgen for two-dimensional observation and X-ray computed tomography (CT) for three-dimensional observation.

On the other hand, the latter, namely, the phase-contrast X-ray imaging system, requires a means for detecting a phase-shift to the above-mentioned system configuration in addition; however, this system is capable of observing biological soft tissues, with extremely high sensitivity, without contrast agents and with low X-ray damage, as compared to the absorption-contrast X-ray imaging system. This is due to the fact that a scattering cross-section that effects the phase-shift is, in terms of light elements, about 1000 times larger than a scattering cross-section that effects the change in the intensity. The phase-shift detecting means include (1) a method using an X-ray interferometer (i.e., an X-ray interference method), as disclosed in Japanese Unexamined Patent Application Publication No. Hei 4-348262; (2) a method utilizing a refraction angle θ of the X-rays which is proportional to spatial differential of the phase-shift (i.e., a refraction-contrast method, diffraction enhanced imaging (DEI)), as disclosed in Japanese Patent Application Publication No. Hei 9-187455; and (3) a method using X-ray Fresnel diffraction. The difference in principle among the above-mentioned methods is that the method (1), namely, the X-ray interference method, is detecting the phase-shift directly, whereas the other methods are detecting the spatial differential of the phase-shift. Description will be outlined below with regard to the methods (1) and (2) concerned deeply with the present invention.

The system for the above-mentioned method (1), namely, the X-ray interference method, is composed of the X-ray interferometer, such as a Bonse-Hart interferometer (such as described in Appl. Phys. Lett. 6, 155 (1965)) or an interferometer by dividing the crystal of this type of interferometer into multiple crystal blocks (such as described in J. Appl. Cryst. 7, 593 (1974)), in addition to the X-ray source, the sample placement mechanism and the detector.

FIG. 1 is a perspective view schematically showing the configuration of the Bonse-Hart interferometer. The Bonse-Hart interferometer includes three wafers (a beam splitter 1, a mirror 2, and an analyzer 3) disposed parallel to one another at regular intervals, and is made of a crystal block formed monolithically of a single crystal ingot. An incident X-ray 4 is split by the first wafer (the beam splitter 1) into two beams 5 and 6, which are thereafter reflected by the second wafer (the mirror 2) and then combined at the third wafer (the analyzer 3) to form two interference beams 7 and 8. When a sample 9 is installed on an optical path of any one of the split beams 5 and 6, a phase-shift p of the beams caused by the sample 9 changes the intensity of the interference beams 7 and 8 by superposition (or interference) of waves. Utilizing this principle, an image (or a phase-map) indicating spatial distribution of the phase-shift p caused by the sample is obtained, by using a method called "sub-fringe", from an intensity distribution image of the interference beams 7 and 8 detected by an image detector or the like. In this instance, using, as the sub-fringe method, a Fourier transform method disclosed in Appl. Opt. 13 (1974) 2693 enables to obtain the phase-map from a single interference image and thus to observe even a phenomenon that changes rapidly with time. Also, imaging systems capable of three-dimensional nondestructive observation using a combination of the phase-contrast imaging method and a typical X-ray CT approach include the system disclosed in Japanese Unexamined Patent Application Publication No. Hei 4-348262. As in the case of the typical X-ray CT, this system involves irradiating a sample with X-rays in multiple different directions, and reconstructs a cross-section image of the sample by computation based on a phase-map acquired for each projection.

The above DEI method (2) obtains the phase shift p, utilizing a phenomenon in which the direction of propagation (or a wavefront) of the X-ray is slightly diverged by refraction as shown in FIG. 2 if the phase shift p is spatially nonuniform when the X-ray passes through a sample that causes the phase shift p. The refraction angle θ of the X-ray caused by the sample is given by Equation (1) as a function of the spatial differential of p:

$$\theta = \frac{\lambda}{2\pi} \frac{dp}{dx} \quad (1)$$

where λ denotes the wavelength of the X-ray. Thus, detection of θ enables to obtain the spatial differential of the phase shift p, and further, the spatial integration enables to obtain the phase shift p.

In a hard X-ray region, the refraction angle θ is generally a very small value of approximately a few μrad. Thus, X-ray diffraction of a flat plate single crystal 10 called an analyzer crystal is utilized for detection of θ (see FIG. 2). When an incident angle $\theta_B$ of the X-ray with respect to the analyzer crystal satisfies diffraction conditions expressed as the following Equation (2):

$$\lambda = 2d \sin \theta_B \quad (2)$$

within a range of angles of a few grad, the incident X-ray is diffracted (or reflected) by the analyzer crystal. Here, d denotes a lattice spacing of diffraction plane. Accordingly, when the direction of propagation of the X-ray is not diverged (θ=0), the incident angle of the X-ray with respect to the analyzer crystal is set so as to satisfy Equation (2), and thereby, intensity I of the diffracted X-ray depends on θ and gets the maximum when θ=0, and decreases with increasing of θ and gets almost zero when θ equals a few μrad. Utilizing this phenomenon, θ, that is, an image, the contrast of which is represented by the amount of spatial differential of the phase-shift, can be obtained from the spatial distribution (or the diffraction image) of the diffraction intensity I, and further, an image (or the phase map) showing the spatial distribution of the phase shift p can be obtained by integration calculation. Incidentally, besides X-ray diffraction based on Bragg-case, a method utilizing X-ray diffraction based on X-ray transmission Laue-case is also developed (see Jpn. J. Appl. Phys. 40 (2001) L844), and recently, a method utilizing a transmitted wave is called a dark field, and a method utilizing a diffracted wave is called a bright field.

As can be seen from FIG. 2, the use of a single diffracted image (or reflected image) alone cannot distinguish between the change in intensity caused by the absorption of the X-ray by the sample and the change in intensity caused by θ, and hence cannot quantitatively determine θ. Thus, generally, the DEI method involves rotating the analyzer crystal in the vicinity of a Bragg angle, and calculating θ from multiple obtained diffracted images. In this instance, rotation methods include (a) a "two-point method" using two angles alone for measurement (see Phys. Med. Biol. 42 (1997) 2015), and (b) a "scan method" using three or more angles for measurement (see Japanese Patent Application Publication No. Hei 9-187455).

The "two-point method" (a) uses two angles which sandwich a Bragg angle $\theta_B$ to obtain an image. If the incident angle of the X-ray on the analyzer crystal is set to an angle at which the diffraction intensity value is half of the peak value ($\theta_B \pm d\theta_D/2$), intensity Ir of the X-ray diffracted by the crystal is given by Equation (3):

$$I_r = I_o R\left(\theta_B \pm \frac{d\theta_D}{2} + \theta\right) \quad (3)$$

where $I_o$ denotes intensity of the incident X-ray, and R denotes reflectance of the analyzer crystal. At the above angle, R is substantially proportional to θ, so that R can be approximated by a second-order Taylor expansion as given by Equation (4).

$$R\left(\theta_B \pm \frac{d\theta_D}{2} + \theta\right) = R\left(\theta_B \pm \frac{d\theta_D}{2} + \theta\right) + \frac{dR}{d\theta}\theta \quad (4)$$

The diffraction intensity ($I_l$ and $I_h$) at a low angle ($\theta_L = \theta_B - d\theta_D/2$) and a high angle ($\theta_H = \theta_B + d\theta_D/2$) are expressed as Equations (5) and (6), respectively, from Equations (3) and (4).

$$I_l = I_o\left(R(\theta_L) + \frac{dR}{d\theta}\theta\right) \quad (5)$$

$$I_h = I_o\left(R(\theta_H) + \frac{dR}{d\theta}\theta\right) \quad (6)$$

Erasing $I_0$ from the above equations leads finally to θ being expressed as Equation (7).

$$\theta = \frac{I_l R(\theta_L) - I_h R(\theta_H)}{I_l \frac{dR}{d\theta}(\theta_H) - I_h \frac{dR}{d\theta}(\theta_L)} \quad (7)$$

Accordingly, the refraction angle θ (x, y) at each point (or pixel) on the sample can be obtained by performing calculation of Equation (7) for each point of $I_1$ and $I_h$ obtained at the above two angles. Also, the phase-map can be obtained by integrating θ (x, y) at each obtained point in a direction horizontal to the sheet of FIG. 3. Note that, if there is a great change in density of the sample and thus a change in θ is greater than an angular width of diffraction (up to $d\theta_D$), the diffraction intensity becomes zero or a value different from the intended value over the diffraction peak, and cannot be detected normally. Thus, the largest dp/dx value detectable with this method is limited by Equation (8).

$$\frac{dp}{dx} = \frac{d\theta_D}{2}\frac{2\pi}{\lambda} \quad (8)$$

The "scan method" (b) involves, as shown in FIG. 4, rotating the analyzer crystal at an angle of the angular width of diffraction (up to $d\theta_D$) or greater in the vicinity of the Bragg angle, and calculating the refraction angle θ from multiple obtained diffracted images (typically, three or more images). This method is characterized in that rotation of the analyzer crystal at a large angle enables detection of θ greater than $d\theta_D/2$, and there is no limitation on a density dynamic range, which is a problem of the method (a).

In this method, the diffraction intensity changes as shown in FIG. 5 with the rotation $\theta_A$ of the analyzer crystal, and thus, the intensity of the diffracted beam of the X-ray that passed through each point (x, y) on the sample has a peak at an angle offset by the refraction angle θ from the Bragg angle $\theta_B$. Thus, the refraction angle θ can be calculated from Equation (9) as the center of the intensity of the diffracted beam:

$$\theta(x, y) = \frac{\sum_n \theta_n I_n(\theta_n, x, y)}{\sum_n I_n(\theta_n, x, y)} \quad (9)$$

where $\theta_n$ denotes each angle of the analyzer crystal, and $I_n(\theta_n)$ denotes the intensity of the diffracted beam obtained at $\theta_n$. Thus, the spatial distribution image (or the phase-map) of the phase shift p can be obtained by integrating θ (x, y) at each obtained point in a direction horizontal to the sheet of FIG. 4, as in the case of the two-point method.

Also, the DEI method can involve rotating the sample with respect to the incident X-ray and nondestructively obtaining the cross-section image of the sample by calculation of reconstruction from the projection image obtained at each angle, as in the existing X-ray CT.

SUMMARY OF THE INVENTION

The X-ray interference method (1) detects a phase shift α caused by the sample as a wrapped value α' (α'=α−Int(α/2π) *2π) wrapped within 0 to 2π, as shown in FIG. 6. Thus, it is required that a method disclosed in Japanese Patent Application Publication No. 2001-153797, or the like be used to perform complicated operation called phase unwrapping and restore the true amount of phase shift α (see FIG. 6). Also, in a region where the shape or inside structure of the sample is complicated and thus the density spatially sharply changes, the refraction angle θ is so large that the X-ray greatly deviates from the original optical path, and that deterioration in visibility of the interference image, disappearance of interference fringes, and the like occur. As a result, a problem arises that the above unwrapping process is not performed normally, and thus, α cannot be restored accurately. To avoid this problem, there is a method that involves soaking a sample in a liquid and reducing a difference in density between the sample and its periphery, as disclosed in Japanese Unexamined Patent Application Publication No. Hei 7-209212; however, this method cannot treat a sharp change in density in the inside, although being able to reduce the influence on the shape.

The both DEI method (2) (the two-point method and the scan method) involves rotating the analyzer crystal in the vicinity of the Bragg angle and thereby obtaining the image. This method is based on a condition that the state of the sample is steady during measurement, and if a change in the state occurs during the measurement, an accurate image cannot be obtained. Thus, this method has the problem of requiring a long measurement time and thus being unable to perform time-resolved observation. Also, if the intensity of the incident X-ray varies with time, the intensity of the image obtained at each angle also varies, and thus, the refraction angle θ cannot be determined accurately, so that the density resolution deteriorates. Further, measurement of a sectional image using the CT requires repeating angular scan several hundred times. However, it is difficult to accurately ensure the angular reproducibility of the analyzer crystal under the influence of drift rotation caused by a temperature and the like.

Summarizing the above, the X-ray interference method can obtain the phase-map from one image by using Fourier transform method and thus takes a short measurement time; however, this method has the problem of narrow density dynamic range. Meanwhile, the DEI method has a wide dynamic range; however, this method has the problem of having to obtain at least two images and thus taking a long measurement time. Against such a background, an object of the present invention is to solve the above problems, and to provide an X-ray imaging system and method capable of performing time-resolved observation in the same density resolution and dynamic range as the DEI method in a short measurement time and also observing the sample with high sensitivity even if the intensity of the incident X-ray varies with time.

The present invention utilizes multiple X-ray diffractions as described in detail below to thereby solve the above problems. The X-ray diffraction is a phenomenon in which the X-ray is diffracted by a crystal lattice plane, and is classified into the Laue-case in which the incident X-ray and the diffracted X-ray lie on different sides of crystal planes (see FIG. 7A) and the Bragg-case in which the incident X-ray and the diffracted X-ray lie on the same side of crystal plane (see FIG. 7B). In the Laue-case and the Bragg-case in which the crystal is extremely thin, the incident X-ray is split into two beams, namely, the transmitted X-ray and the diffracted X-ray.

In the X-ray diffraction in the Laue-case, the intensity $I_g$ of the diffracted X-ray is given by Equation (10) based on dynamical theory of X-ray diffraction, and the intensity $I_h$ of the transmitted X-ray is given by Equation (11).

$$\frac{I_g}{I_o} = \frac{1}{2(W^2 + 1)} \tag{10}$$

$$\frac{I_h}{I_o} = 1 - \frac{1}{2(W^2 + 1)} \tag{11}$$

Here, the absorption of the X-ray by the crystal is ignored. Also, $I_o$ denotes the intensity of the incident X-ray, and W denotes a variable given by the following Equation (12):

$$W = \frac{d\theta \sin 2\theta_B}{|\chi_g|} \tag{12}$$

where $d\theta$ denotes a deviation from the Bragg angle, and $\chi_g$ denotes electric susceptibility, and thus, $I_g$ and $I_h$ depend on $d\theta$, i.e., the deviation of the incident angle from the Bragg angle.

FIG. 8 shows the calculated $I_g$ and $I_h$ of a lattice plane (220) of a silicon crystal, based on Equations (10) and (11). The horizontal axis indicates the deviation of the incident angle from the Bragg angle, and the vertical axis indicates the intensity of the X-ray. Energy of the X-ray was set to 35 keV, and the thickness of the crystal was set to 1 mm. From this drawing, it can be seen that the X-ray is diffracted only when the incident angle of the X-ray is in the vicinity of the Bragg angle, and other X-rays are transmitted.

On the other hand, in the X-ray diffraction in the Bragg-case, the intensity $I_g'$ of the diffracted X-ray and the intensity $I_h'$ of the transmitted. X-ray are given by Equations (13) and (14) based on dynamical theory of X-ray diffraction, as in the case of the Laue-case.

$$\frac{I_g}{I_o} = \begin{cases} \left(|W| - \sqrt{W^2 - 1}\right)^2 : |W| \geq 1 \\ 1 : |W| \leq 1 \end{cases} \tag{13}$$

$$\frac{I_h}{I_o} = \begin{cases} 1 - \left(|W| - \sqrt{W^2 - 1}\right)^2 : |W| \geq 1 \\ 0 : |W| \leq 1 \end{cases} \tag{14}$$

Here, W is given by Equation (12), and both $I_g'$ and $I_h'$ depend on the incident angle. FIG. 9 shows the calculated results of $I_g'$ and $I_h'$ at the lattice plane (220) of the silicon crystal, based on Equations (13) and (14). The horizontal axis indicates the deviation of the incident angle from the Bragg angle, and the vertical axis indicates the intensity of the X-ray. Energy of the X-ray was set to 35 keV, and the thickness of the crystal was set to 1 mm. From this figure, it can be seen that the X-ray is diffracted only when the incident angle of the X-ray is in the vicinity of the Bragg angle, and other X-rays are transmitted, as in the case of the Laue-case.

Discussion will now be made with regard to Laue-case X-ray diffraction using a series arrangement of two crystal wafers one of which relative angle is deviated by $\Delta\omega$ as shown in FIG. 10. In this instance, the intensity $I_1$ of the X-ray diffracted by a first crystal wafer 11 is given by Equation (10). Moreover, the intensity $I_2$ of the X-ray diffracted by a second crystal wafer 12 is given by Equation (15), because it is the product of Equations (10) and (11). Further, the intensity $I_t$ of the X-ray that has passed through the second crystal wafer is given by Equation (16) from Equation (11).

$$\frac{I_2}{I_o} = \frac{1}{2((W+\Delta\omega)^2+1)} - \frac{1}{4((W+\Delta\omega)^2+1)(W^2+1)} \quad (15)$$

$$\frac{I_t}{I_o} = \left(1 - \frac{1}{2(W^2+1)}\right)\left(1 - \frac{1}{2((W+\Delta\omega)^2+1)}\right) \quad (16)$$

FIG. 11 shows the calculated results of $I_1$, $I_2$ and $I_t$ under the same calculation conditions as those shown in FIG. 8 and under the condition that $\Delta\omega=10$ μrad. From these results, it can be seen that $I_1$ is intense in an angular range around $\theta_B$; $I_2$, in an angular range around $\theta_B+\Delta\omega$; and $I_t$, in an angular range excluding $\theta_B$ and $\theta_B+\Delta\omega$. As apparent from the arrangement shown in FIG. 10, $I_1$, $I_2$ and $I_t$ can be detected at a time. Consequently, two images, which have been heretofore obtained in sequence by scanning the angle of the analyzer crystal at the angles $\theta_B$ and $\theta_B+\Delta\omega$, can be obtained at a time. Accordingly, when $\Delta\omega$ is set to $d\theta_D$ and the angle of the first crystal is set to $\theta_B-d\theta_D/2$, the above-mentioned two-point method can be used to obtain the images $I_h$ and $I_1$ at a time, and this eliminates the need for the rotational scan of the analyzer crystal. Also, for the scan method, setting of $\Delta\omega$ to around $d\theta_D/5$ enables obtaining the images of the low and high angles of the diffraction peak at a time, and thus enables reducing the number of scans by half or more. Incidentally, it is also applicability for the Bragg case in which the thickness of the crystal is extremely thin.

Although description has been given above with regard to an instance where two crystal wafers are used, n crystal wafers may naturally be used (where n denotes an integer equal to or more than three). In this instance, the deviation of the angle between crystals by $d\theta_D/(n-1)$ makes it possible to obtain n diffracted images at $\theta_n$ in Equation (9) at a time. Accordingly, this eliminates the need for scanning the analyzer crystal from the scan method.

As can be seen from the above, the utilization of multiple X-ray diffractions eliminates the need for scanning the analyzer crystal, and thus enables time-resolved observation over a wide density dynamic range and also enables high-sensitivity observation of the sample even if the intensity of the incident X-ray varies with time.

The present invention enables time-resolved observation over a wide density dynamic range and also enables high-sensitivity observation of an image using the spatial phase-shift of the sample as the contrast even if the intensity of the incident X-ray varies with time.

DETAILED DESCRIPTION OF THE PREFERRED EMBODIMENTS

Figure 1:
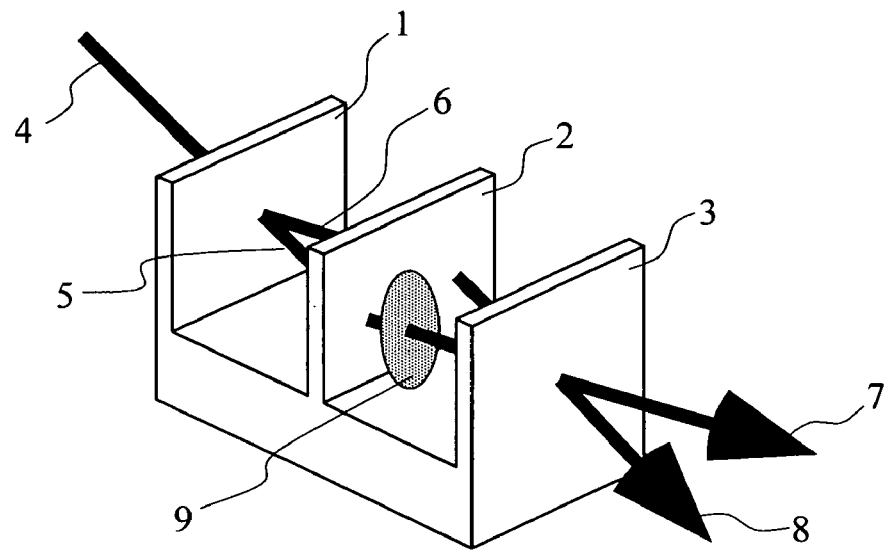
FIG. 1 is a view showing a Bonse-Hart interferometer.
Figure 2:
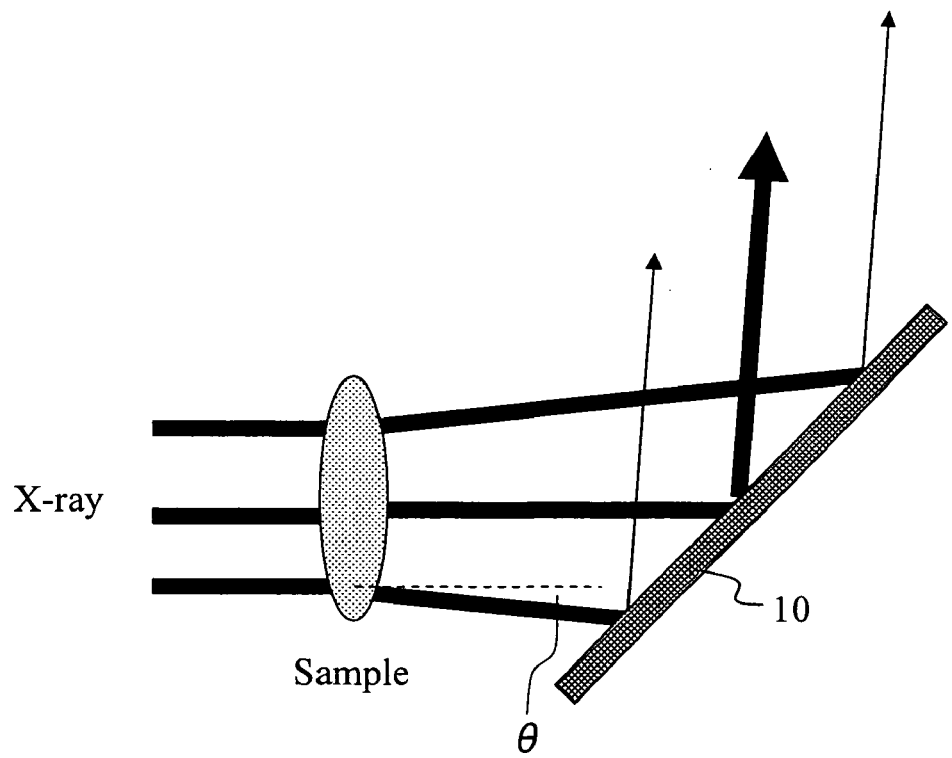
FIG. 2 is a view showing refraction of X-rays by a sample and diffraction of the X-rays by an analyzer crystal.

Description will be given below with reference to the drawings with regard to embodiments of the present invention. In the drawings, parts having the same function are indicated by the same reference numerals, and repeated description thereof will be omitted.

First Embodiment

Figure 12:
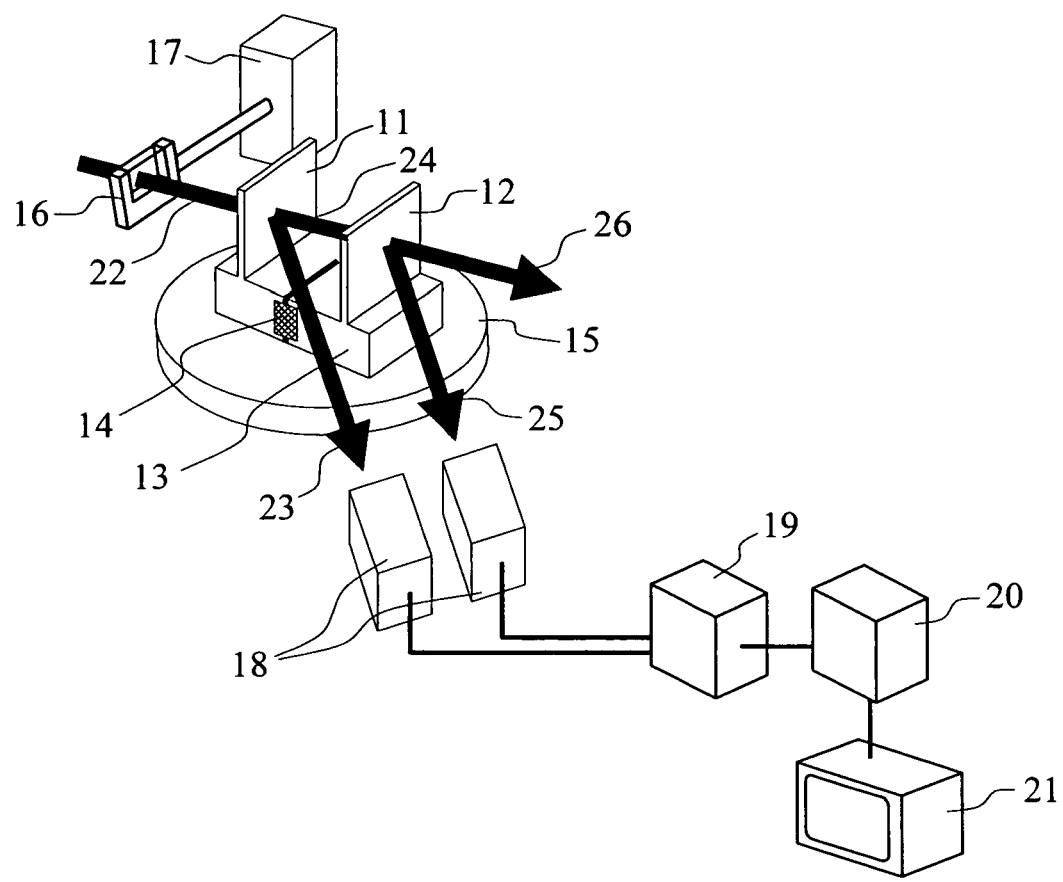
FIG. 12 is a view showing a configuration example of an X-ray imaging system according to the present invention.

FIG. 12 is a view showing the configuration of an example of an X-ray imaging system according to the present invention. The X-ray imaging system is composed of a single crystal block 13 formed monolithically having two crystal wafers 11 and 12, a rotational mechanism 14, a crystal block positioning mechanism 15, a sample holder 16, a sample holder positioning mechanism 17, an X-ray imager 18, a controller 19, a processing unit 20, and a display device 21.

X-rays 22 that have passed through a sample enter the first crystal wafer 11 of the single crystal block, only the X-rays that satisfy a given angle condition are diffracted to form diffracted X-rays 23, and the other X-rays pass through the first crystal wafer to form transmitted X-rays 24. The transmitted X-rays 24 further enter the second crystal wafer 12, only the X-rays that satisfy a given angle condition are diffracted to form diffracted X-rays 25, and the other X-rays pass through the second crystal wafer to form transmitted X-rays 26. The diffracted X-rays are detected by the X-ray imagers 18, respectively. Incidentally, the use of a two-dimensional X-ray imager as the X-ray imager 18 enables detection of a two-dimensional image of the sample without the need for spatial scan of X-ray beams. Further, when the crystal wafers 11 and 12 are disposed at narrow spaced intervals, so that the diffracted X-rays are arranged substantially side by side as shown in FIG. 12, an X-ray imager with a large field of view can be used alone to detect both X-rays at a time. With such a configuration, a control system can be further simplified.

When the sample is placed in an optical path of the incident X-ray beam by use of the sample holder 16 positioned by the sample holder positioning mechanism 17, the direction of propagation of the X-ray beams 22 that have passed through the sample is deviated by a refraction angle θ by the refraction effect of the sample. As a result, the incident angle to the crystal wafers 11 and 12 changes, and thus, the diffracted X-rays 23 and 25 also change in intensity according to the change in the angle. For this reason, the refraction angle caused by the sample can be detected from the change in the intensity of the diffracted X-rays.

Figure 3:
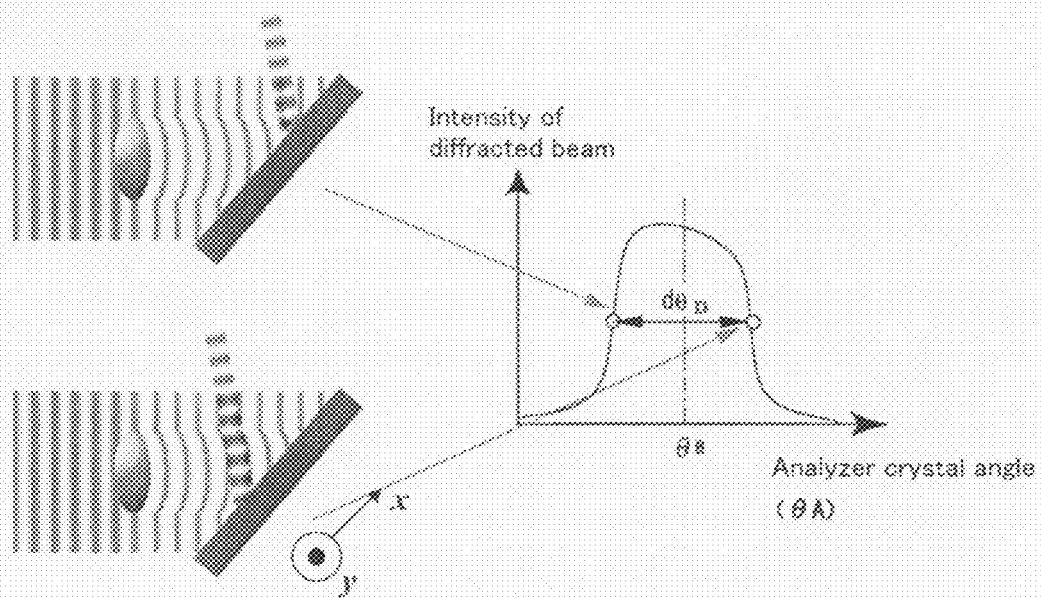
FIG. 3 is a view showing the angle of the analyzer crystal in a two-point method.
Figure 4:
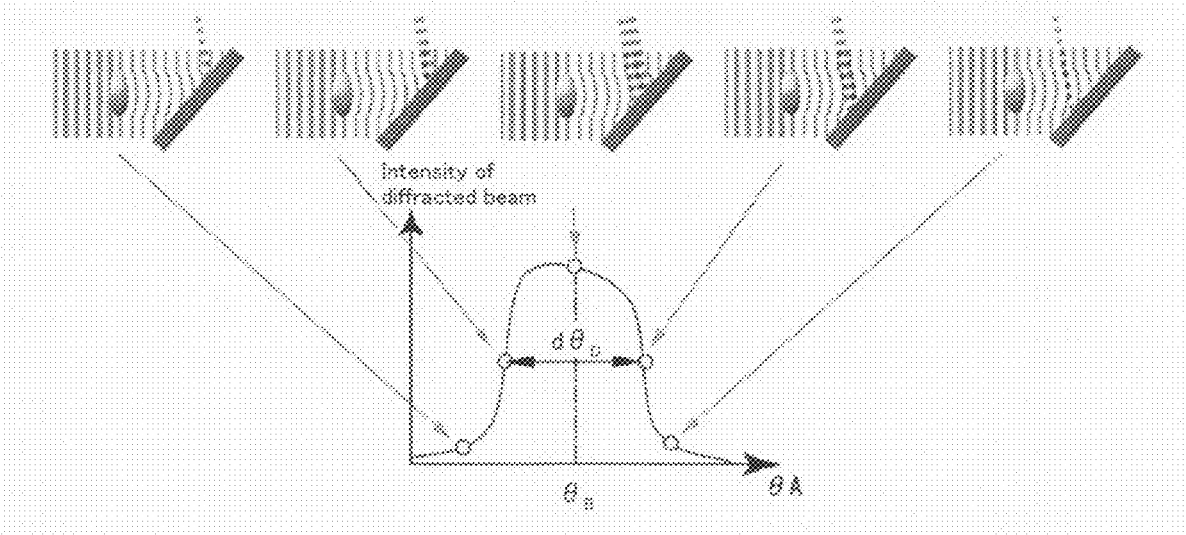
FIG. 4 is a view showing the angle of the analyzer crystal in a scan method.
Figure 5:
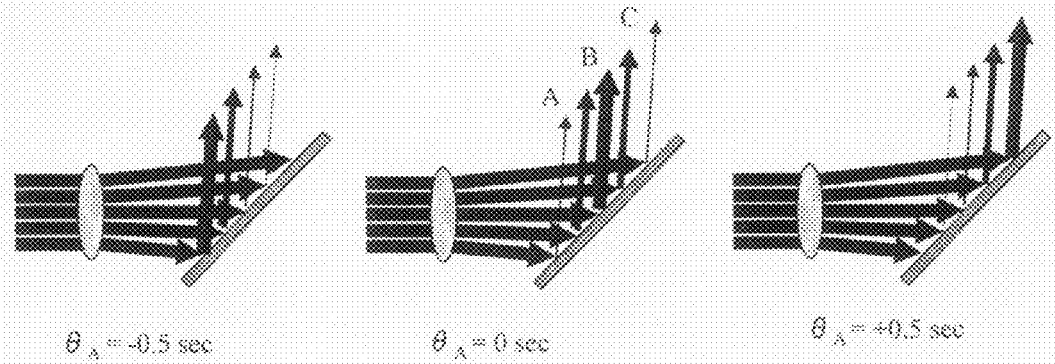
FIG. 5 is a view showing diffraction intensity at each sample point in the scan method.
Figure 5:
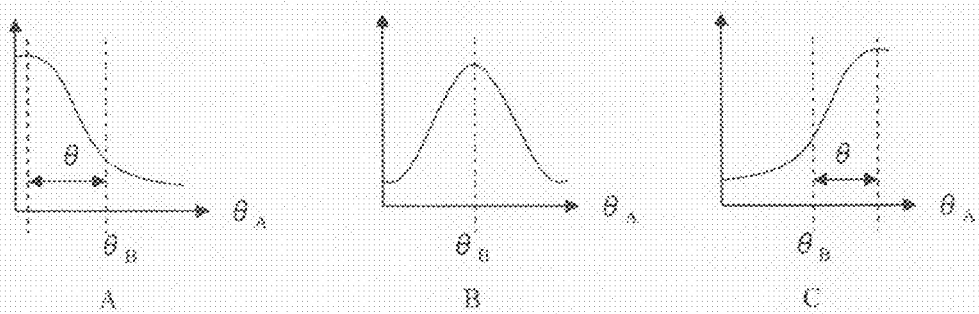
Figure 6:
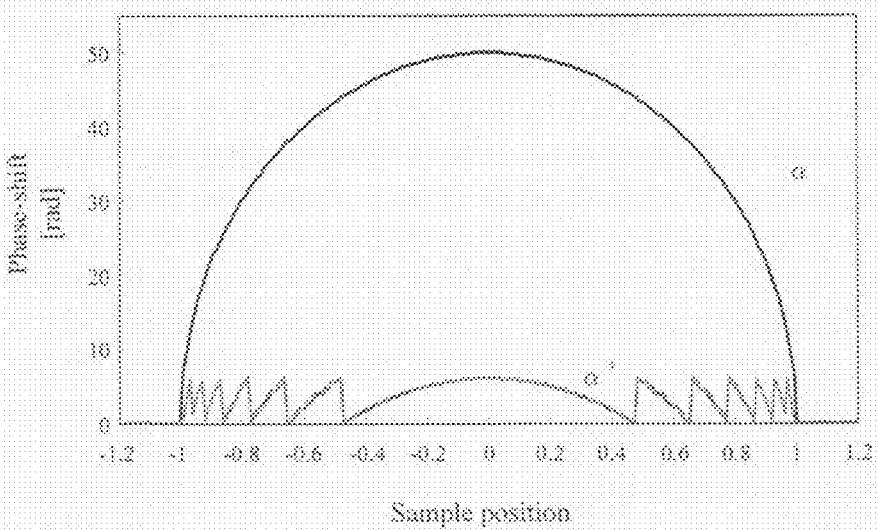
FIG. 6 is a view showing a wrapped phase α' and an unwrapped phase α.
Figure 7A:
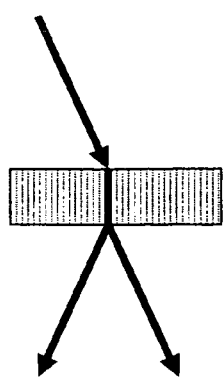
FIGS. 7A and 7B are views showing the relationship between the X-ray and the crystal for Laue-case X-ray diffraction and Bragg-case X-ray diffraction, respectively.
Figure 7B:
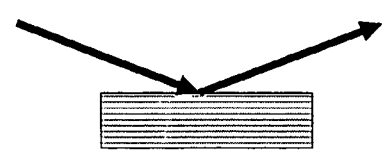
Figure 8:
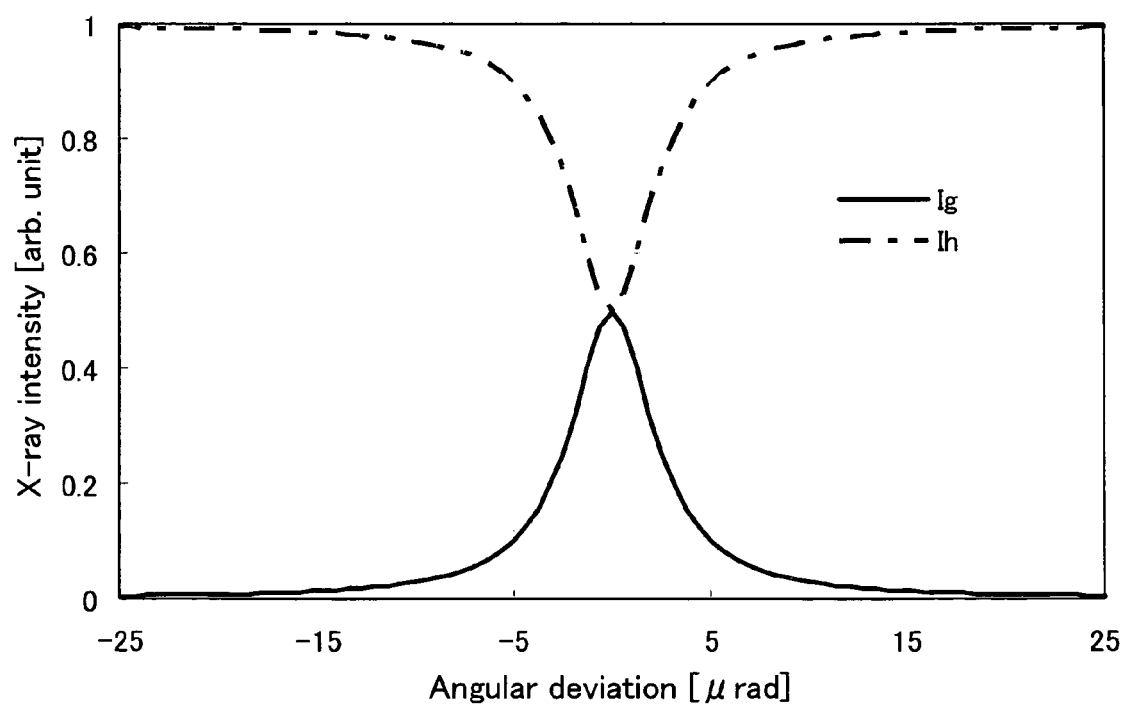
FIG. 8 is a graph showing a calculation example of the intensity of a diffracted X-ray and a transmitted X-ray for the Laue-case X-ray diffraction.
Figure 9:
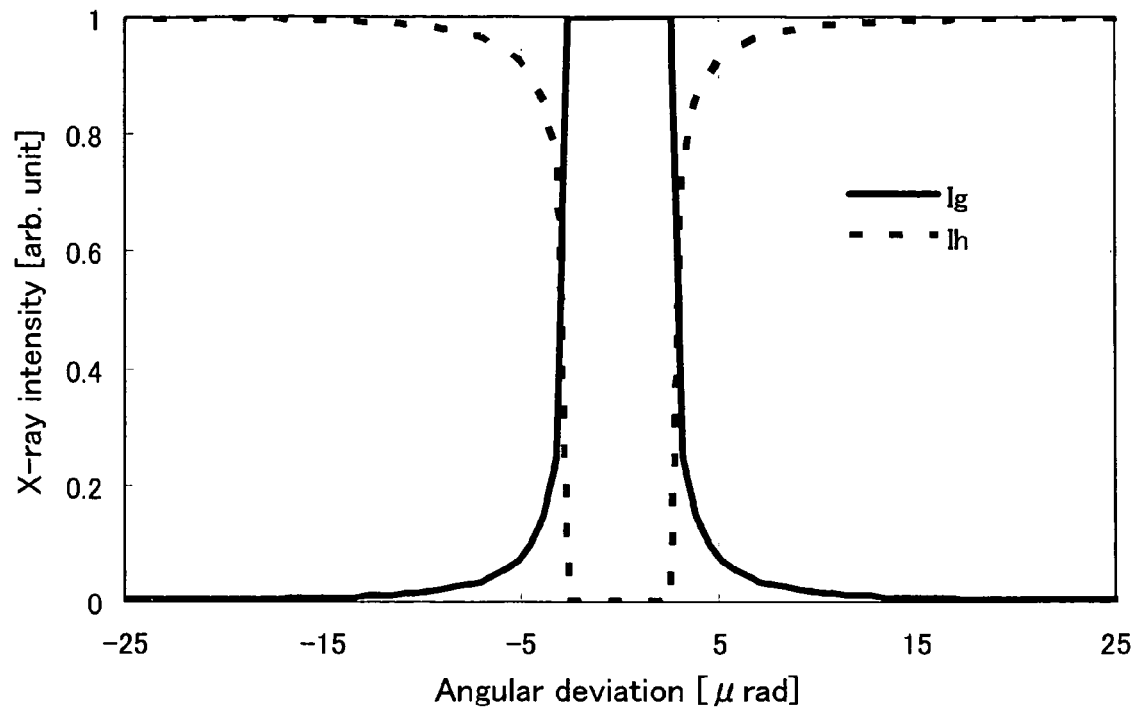
FIG. 9 is a graph showing a calculation example of the intensity of a diffracted X-ray and a transmitted X-ray for the Bragg-case X-ray diffraction.
Figure 10:
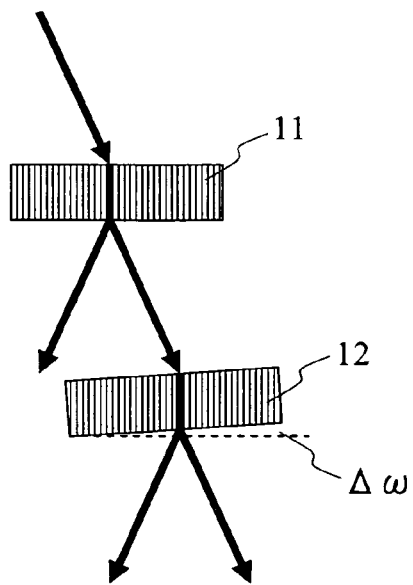
FIG. 10 is a view showing the arrangement of the analyzer crystals of the present invention.
Figure 11:
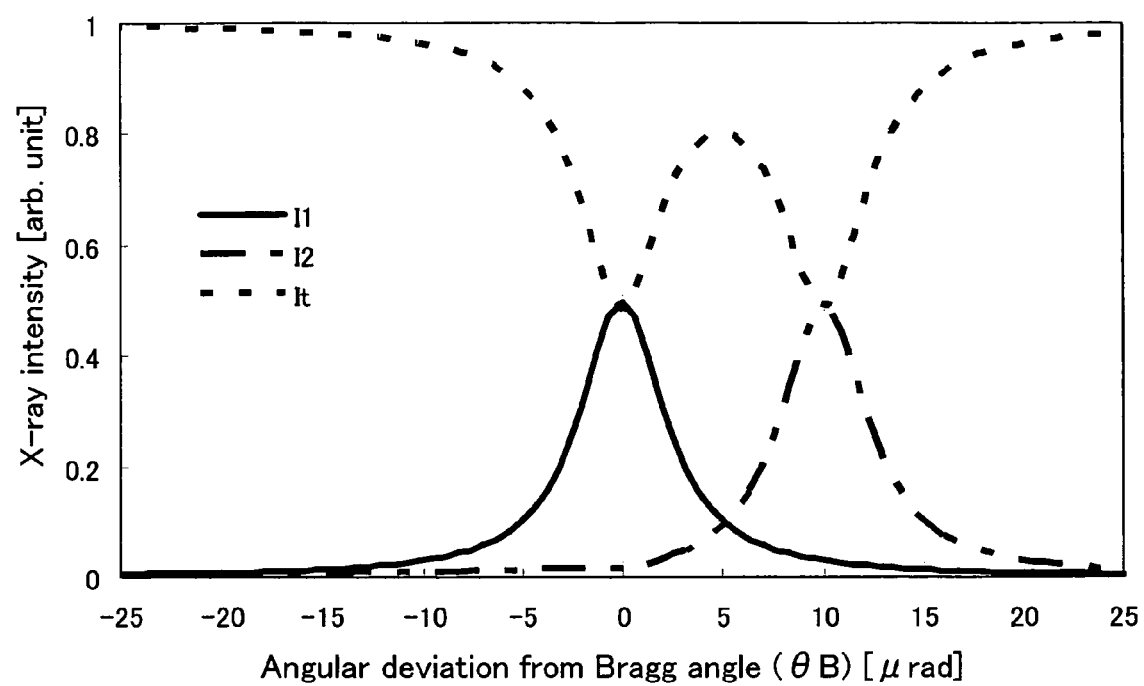
FIG. 11 is a graph showing a calculation example of the intensity of the diffracted X-rays and the transmitted X-rays.

When the angle of the crystal wafer 11 is preset to an angle that reduces the diffraction intensity by half (or the lower angle than the Bragg angle) as shown in FIG. 3, the intensity $I_{r1}$ of the diffracted X-ray given by Equation (5) can be obtained. Incidentally, at this time, the diffraction intensity is most sensitive to the refraction angle. Also, when the angle of the crystal wafer 12 is preset to another angle that reduces the diffraction intensity by half (or the higher angle than the Bragg angle) by use of the rotational mechanism 14, the intensity $I_{r2}$ of the diffracted X-ray given by Equation (6) can also be obtained. Thereby, the refraction angle of the X-ray caused by the sample can be obtained from the detected $I_{r1}$ and $I_{r2}$, by means of the two-point method, using Equation (7). Further, integration enables to obtain the phase-map of the sample.

Further, in addition to the above-mentioned measurement, when the crystal block positioning mechanism 15 is used to obtain multiple images while rotationally scanning the single crystal block 13, an angular difference between the crystal wafers 11 and 12 can be set to an angular width of diffraction by the rotational mechanism 14 so that the diffracted X-rays at the lower angle than the Bragg angle and the diffracted X-rays at the higher angle than the Bragg angle can be detected at a time by the crystal wafers 11 and 12, respectively. Accordingly, in the scan method, the number of angular scans that have been heretofore required n times can be reduced by half, i.e. to n/2 times, and this enables a reduction in measurement time and a reduction in X-ray damage. Incidentally, the refraction angle caused by the sample can be obtained from multiple diffracted X-ray images acquired through angular scan as mentioned above, in the same manner as hitherto, by Equation (9).

The diffraction plane of the crystal wafer is determined based on the energy of X-rays to be used, the size of the sample, a required density resolution, and a required dynamic range. If a large observation field is required, a low-order lattice plane having a large Bragg angle can be selected. If the sufficient density resolution is required, a high-order lattice plane having the intensity curve shown in FIG. 3 with a sharp gradient can be selected. If a wide dynamic range is required, a low-order lattice plane having a wide diffraction width can be selected.

Figure 13:
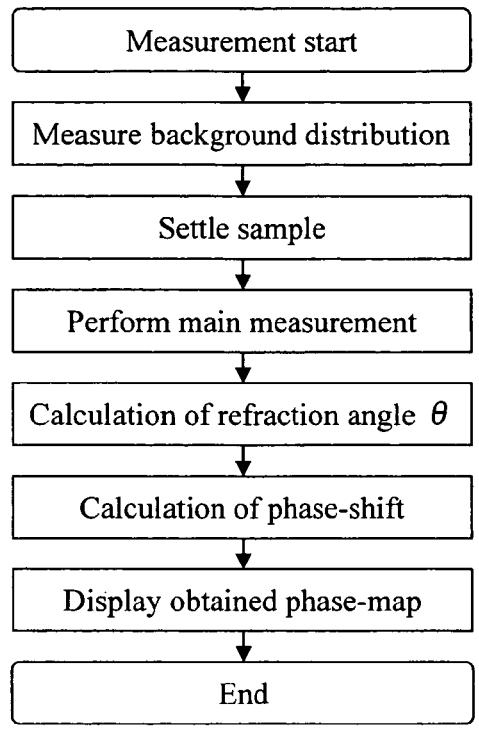
FIG. 13 is a chart showing a measurement procedure for removing strain of a refractive index of a background distribution.

If crystal strain or the like remains in the crystal wafers 11 and 12 that form an angular analyzer, the diffraction condition becomes spatially nonuniform, and thus, accurate observation of the sample image becomes impossible. Thus, the crystal wafer can be subjected to mechanochemical polishing or the like on the surface thereof to form the crystal wafer with little strain and high flatness for use. However, even after the above process is finished, the strain cannot be completely removed. Thus, a procedure shown in FIG. 13 is used to remove a nonuniform distribution (or a background refraction angle) of the diffraction condition (or the Bragg angle) that forms a background and thereby detect the refraction angle formed only by the sample.

(1) Prior to placement of the sample, the background refraction angle is obtained by the same method as the present measurement (the measurement of the background distribution).

(2) The sample is placed in an optical path by use of the sample holder 16 and the sample holder positioning mechanism 17.

(3) The distribution of the sum of the refraction angle of the background and that of the sample is obtained.

(4) The distribution image of the refraction angle caused by the sample is obtained from the distribution image of the refraction angle obtained in step (1) and (3) by subjecting the background refraction angle to a subtraction process. Further, an integration calculation is performed to obtain the phase-map of the sample (or the spatial distribution image of the phase of the sample).

Angle control of the crystal wafer is extremely important since the angular difference of the extremely slight refraction angle is detected. If the crystal wafer drifts rotationally during measurement, the refraction angle cannot be obtained accurately. Thus, the first embodiment uses a precise positioning table using a tangential bar system as the crystal block positioning mechanism 15. Employing this mechanical mechanism enables achieving a rotational positioning accuracy of 1/100 arc second or less and a drift of 1/10 arc second or less.

Figure 14A:
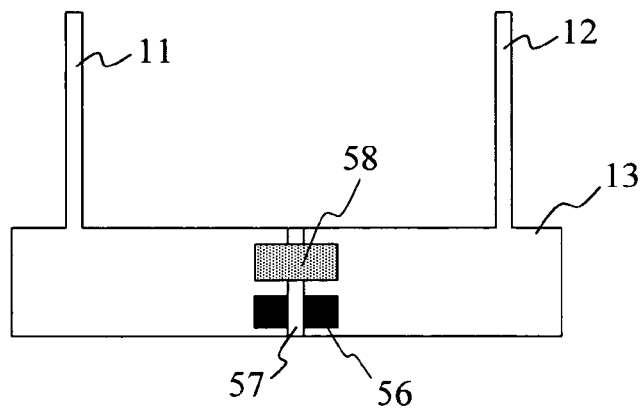
FIGS. 14A and 14B are views showing a detailed example of crystal wafers and a rotational mechanism.
Figure 14B:
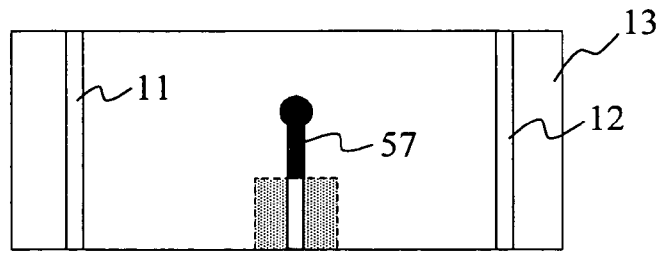

It is also required that the angular difference between the crystal wafers 11 and 12 be controlled with an extremely high accuracy of approximately a few seconds. An example of the rotational mechanism 14 for this purpose is shown in FIGS. 14A and 14B. FIG. 14A is a front view of the single crystal block, and FIG. 14B is a plan view thereof. Here, a notch 57 is cut in the single crystal block 13 that support the two crystal wafers 11 and 12, and the interval of the notch is opened or closed by a piezo 58 to thereby adjust the angular difference. The notch 57 extends from the lateral side of the single crystal block between the two crystal wafers 11 and 12, and the piezo 58 is interposed at an open end of the notch. When the depth of the notch is set to 50 mm and the accuracy of expansion and contraction of the piezo is set to 10 nm, an angular difference of 0.04 arc second can be controlled. Incidentally, in order to reduce the rotational drift of the angular difference over a long time by relaxation of stress of the piezo 58 or the like, a measuring mechanism 56 using a capacitance sensor or a laser may be built in as shown in FIG. 14A, and active control for controlling a voltage applied to the piezo 58 so as to offset the drift may be used.

As the X-ray imager 18, an X-ray film may be used, or a combination of a scintillator, a focusing optical system (e.g., a lens or an optical fiber) and a CCD camera or the like may be used. The latter enables high-accuracy measurement with high efficiency of X-ray detection, in real time, in a short measurement time. Also, multiple X-ray imagers may be prepared to measure transmitted X-rays besides diffracted X-rays and thereby detect all other undiffracted X-rays. The use of the transmitted X-rays for calculation enables detection with higher accuracy.

As described above, the present invention enables detection of the spatial distribution image of the refraction angle caused by the sample and phase-map, without performing the angle scan of the analyzer crystal (i.e., the crystal wafers 11 and 12) if the two-point method is used, or by doing scans, the number of which is half of the number of scans that has been heretofore done, if the scan method is used. This enables observation of the transmitted image of the sample with high sensitivity, in a short measurement time, with low X-ray damage, without consideration of fluctuations in the incident X-ray intensity.

Second Embodiment

In the first embodiment, the Laue-case X-ray diffraction is used to split X-rays. The X-ray in the crystal wafer of the Laue-case X-ray diffraction is spread by the influence of a phenomenon called "Borrmann fan." Thus, the X-ray beam is blurred, resulting in deterioration in the spatial resolution. Here given is an embodiment in which the Bragg-case X-ray diffraction is employed to reduce the deterioration in the spatial resolution due to the above-mentioned phenomenon.

Figure 15:
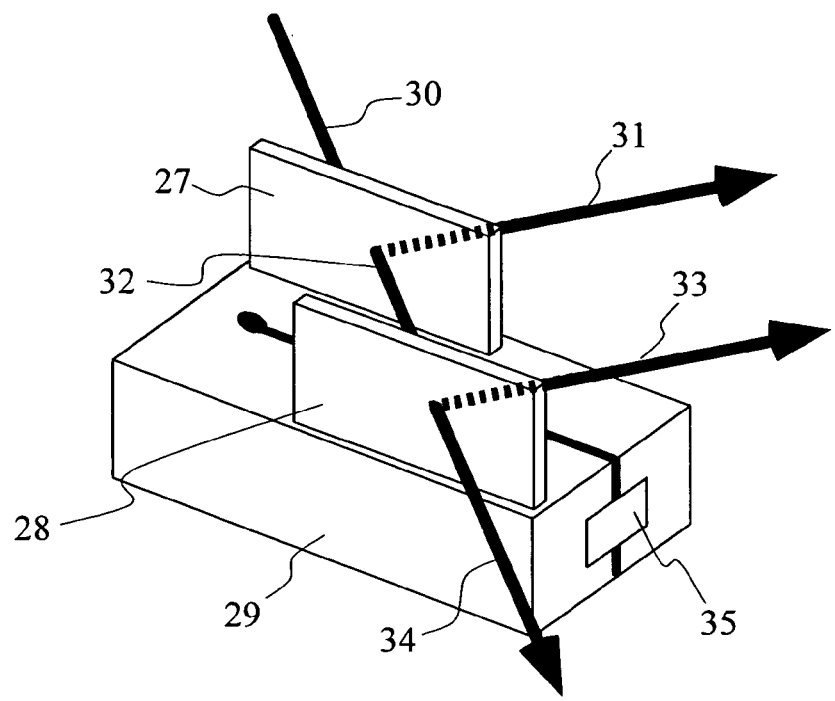
FIG. 15 is a view showing a detailed example of the crystal wafers and the rotational mechanism.

FIG. 15 shows details of crystal wafers 27 and 28 and a single crystal block 29 for use in the second embodiment. Incidentally, the configuration other than the crystal wafers 27 and 28 and the single crystal block 29 is the same as that of the first embodiment. X-rays 30 that have passed through the sample enter the crystal wafer 27, and by the Bragg-case X-ray diffraction, the X-rays that satisfy a given angular range are reflected by diffraction to form diffracted X-rays 31, and the other X-rays pass through the crystal wafer to form transmitted X-rays 32. Further, the transmitted X-rays 32 enter the second crystal wafer 28, and by the Bragg-case X-ray diffraction, only the X-rays that satisfy a given angle condition are diffracted to form diffracted X-rays 33, and the other X-rays pass through the crystal wafer to form transmitted X-rays 34. The diffracted X-rays are detected by the X-ray imagers.

As in the case of the first embodiment, when the angle of the crystal wafer 27 is preset to an angle that reduces the diffraction intensity by half (or the lower angle than the Bragg angle), the intensity $I_{r1}$ of the diffracted X-rays given by Equation (5) is obtained. Also, when the angle of the crystal wafer 28 is preset to another angle that reduces the diffraction intensity by half (or the higher angle than the Bragg angle) by use of a rotational mechanism 35, the intensity $I_{r2}$ of the diffracted X-rays given by Equation (6) may also be obtained. Thereby, the refraction angle of the X-ray caused by the sample can be detected from the detected $I_{r1}$ and $I_{r2}$, by means of the two-point method, using Equation (7). Further, integration enables to obtain the phase-map of the sample.

In addition to the above-mentioned measurement, to obtain multiple images while rotationally scanning the single crystal block, an angular difference between the crystal wafers 27 and 28 can be set to an angular width of diffraction by the rotational mechanism 35 so that the diffracted X-rays at the lower angle than the Bragg angle and the diffracted X-rays at the higher angle than the Bragg angle can be detected at a time by the crystal wafers 27 and 28, respectively. Thus, in the scan method, the number of angular scans that have been heretofore required n times can be reduced by half, i.e. to n/2 times, and this enables a reduction in measurement time and a reduction in X-ray damage. Incidentally, the refraction angle caused by the sample can be obtained from multiple diffracted X-ray images $\theta_n$ obtained through angular scan as mentioned above, in the same manner as hitherto, by Equation (9).

A method for selection of the diffraction plane, a method for removing the nonuniform distribution (or the background refraction angle) of the diffraction condition (or the Bragg angle) that is the background, and the positioning table, which are the same as those of the first embodiment, can be used.

As described above, the second embodiment can utilize the Bragg-case X-ray diffraction to detect the spatial distribution image of the refraction angle caused by the sample and phase-map, without performing the angular scan of the analyzer crystal (i.e., the crystal wafers 27 and 28) if the two-point method is used, or by doing scans, the number of which is half of the number of scans that has been heretofore done, if the scan method is used. This enables observation of the transmitted image of the sample with high spatial resolution and with high sensitivity, in a short measurement time, with low X-ray damage, and without consideration of fluctuations in the incident X-ray intensity.

Third Embodiment

Figure 16:
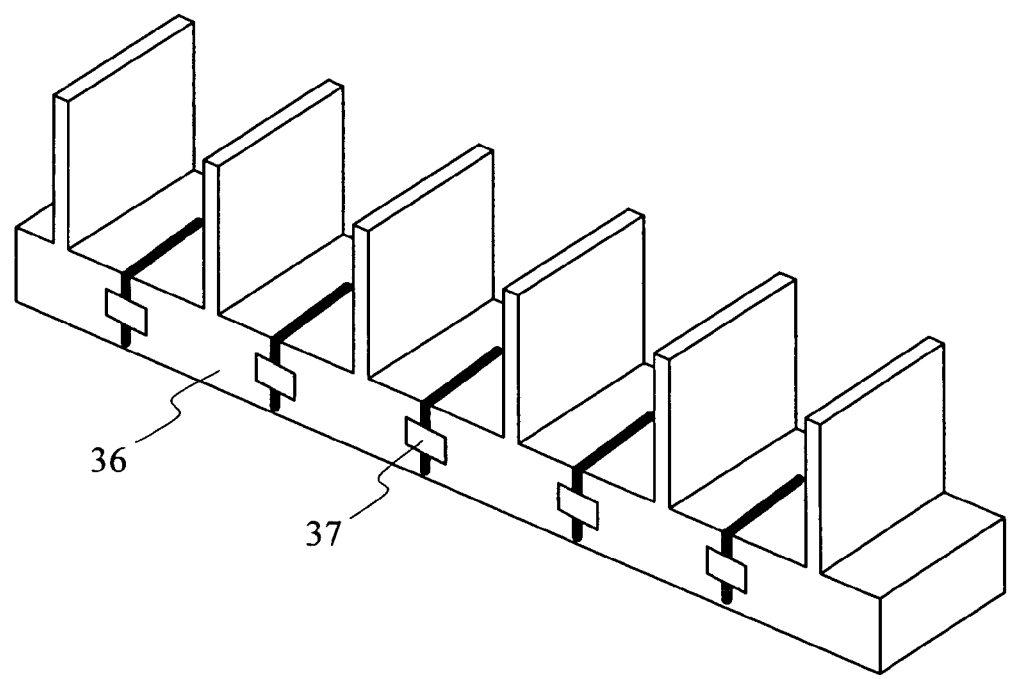
FIG. 16 is a view showing a detailed example of the crystal wafers and the rotational mechanism.

Since the first and second embodiments use two crystal wafers, the "scan method" requires the rotational scan of the single crystal block mounting the crystal wafers. The scan angle width of the rotational scan is a few seconds and the angular step width is of approximately 1/10 arc second, and thus, the rotational mechanism for the crystal block requires high positioning and repeating accuracy. In addition, there is another problem that a long measurement time is required and thus the application to time-resolved observation is difficult. Here given is an embodiment in which a single crystal block 36 mounting n crystal wafers is employed to eliminate the need for the rotational scan of the single crystal block, as shown in FIG. 16. Incidentally, the basic configuration other than the single crystal block mounting the crystal wafers is the same as that of the first embodiment.

As in the case of the first embodiment, only X-rays that satisfy a given angle condition are diffracted to form diffracted X-rays $I_n$, and the other X-rays pass through the crystal wafer. Since the crystal wafers mounted on the single crystal block are arranged in series in the direction of travel of the transmitted X-rays, the X-rays that have passed through the upstream crystal wafer continuously enter the next crystal wafer, and in the same manner, only X-rays that satisfy a given angle condition are diffracted to form diffracted X-rays $I_n$, and the other X-rays pass through the crystal wafer. In the third embodiment, the n crystal wafers are arranged, and thus, this phenomenon is repeated n times. At this time, when the angular difference $\Delta\omega$ between the crystal wafers is adjusted to about $2d\theta_D/n$ by use of a rotational mechanism 37, the diffracted X-ray image In obtained by the crystal wafers is identical to the diffracted X-ray image $I_n$ obtained at each angle $\theta_n$ by scanning one analyzer crystal. Thus, the diffracted X-ray image obtained by the crystal wafers, detected at a time, can be substituted into Equation (9) to obtain the refraction angle without performing n rotational scans of the crystal wafers. Further, the phase-map of the sample can be obtained by integration process using obtained refraction angles. Incidentally, the spatial nonuniformity of the diffraction condition due to the crystal strain or the like remaining on the crystal wafers can be removed by the subtraction of the refraction angle distribution obtained according to the presence or absence of the sample, as in the case of the first embodiment. In FIG. 16, the Laue-case X-ray diffraction is used for beam splitting; however, the Bragg-case X-ray diffraction may also be used as is the case with the second embodiment. In this instance, the blurry of beam due to the Borrmann fan can be reduced, so that the spatial resolution can be improved.

The rotational mechanism 37 for adjusting the angular difference between the crystal wafers requires high angular accuracy, as in the case of the first embodiment. Thus, as in the case of the first embodiment, a notch is cut in the single crystal block that support the crystal wafers, and the interval of the notch is opened or closed by a piezo to thereby adjust the angular difference. Also, in order to reduce the rotational drift of the angular difference over a long time by relaxation of stress of the piezo or the like, a measuring mechanism using a capacitance sensor or a laser may be built in, and active control for controlling a voltage applied to the piezo so as to reduce the drift may also be used.

As described above, the third embodiment enables detecting the spatial distribution image of the refraction angle caused by the sample and phase-map, without performing the angular scan of the single crystal block which mounts the crystal wafers. This enables observation of the transmitted image of the sample with high sensitivity, in a short measurement time, with low X-ray damage, and without consideration of fluctuations in the incident X-ray intensity.

Fourth Embodiment

Figure 17:
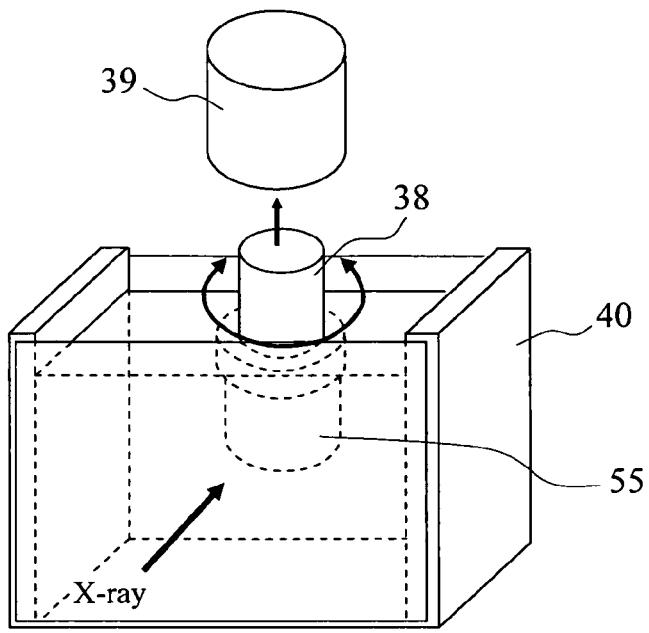
FIG. 17 is a view showing an example of a sample holder and a sample rotating mechanism.

The first to third embodiments can measure only the image that has passed through the sample (the transmitted image). Here given is an embodiment capable of nondestructive observation of the inside of the sample. The system is the same as those of the first to third embodiments, except for a sample holder 38 and a sample rotating mechanism 39. In the fourth embodiment, as shown in FIG. 17, a sample 55 is fixed to the sample holder 38, and can be rotated in a direction (x and z) perpendicular to the optical axis by the sample rotating mechanism 39. Also, in order to reduce the influence of the shape of the sample, the sample may also be immersed for measurement in a sample cell 40 filled with a liquid whose density is close to that of the sample.

Figure 18:
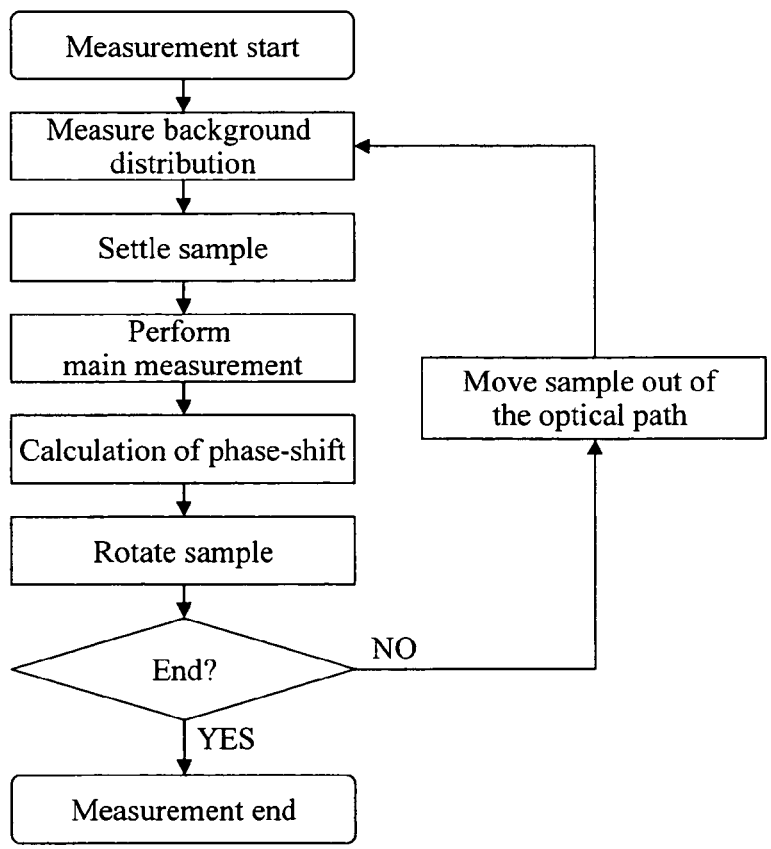
FIG. 18 is a chart showing a measurement procedure.

In the fourth embodiment, as shown in FIG. 18, the following procedure (1) to (3) is performed for the measurement.

(1) Obtain the refraction angle $\theta$ caused by the sample by using the procedure shown in FIG. 13 (i.e., the measurement of the background distribution, the placement of the sample, and the main measurement).

(2) Rotate the sample by $\Delta r$ using the sample rotating mechanism 39.

(3) Repeat the procedures (1) and (2) by the number n of required steps ($=180°/\Delta r$).

(4) Further, in order to improve the accuracy of measurement, the sample may be withdrawn from the optical path, and after the measurement of the background distribution, the procedures (1) to (3) may be repeated required times.

Then, after the measurement, a phase projection image is obtained by integration calculation of the spatial distribution image of the refraction angle $\theta$ acquired at each angle, and further, a sectional image of the sample of phase-contrast is reconstructed from the phase projection image by calculation using reconstruction algorism such as a filtered back projection method. The phase-contrast sectional image obtained through the calculation is displayed on a display unit for example under an operator command or the like. Here, as a method for obtaining the phase-map at each angle, the same method as the first embodiment for the two-point method or the same method as the second embodiment for the scan method may be used for measurement and calculation. Also, the Laue-case X-ray diffraction or the Bragg-case X-ray diffraction may be used for beam splitting.

As described above, the fourth embodiment enables detection of the sectional image of the sample using as the contrast the phase caused by the sample, and thus enables nondestructive observation of the internal structure of the sample with high sensitivity, in a short measurement time, with low X-ray damage, and without consideration of fluctuations in the incident X-ray intensity or the like.

Fifth Embodiment

The crystal wafers for use in the first to fourth embodiments are monolithically formed on the single crystal block, and thus, the size thereof (or a field of view) is limited by the diameter of the crystal ingot that forms a matrix of the single crystal block, which makes it difficult to ensure a size of 2 by 2 centimeters square or more. Here given is an example of an imaging system in which crystal wafers formed on multiple crystal blocks are used to enable ensuring a field of view of 2 cm or more.

Figure 19:
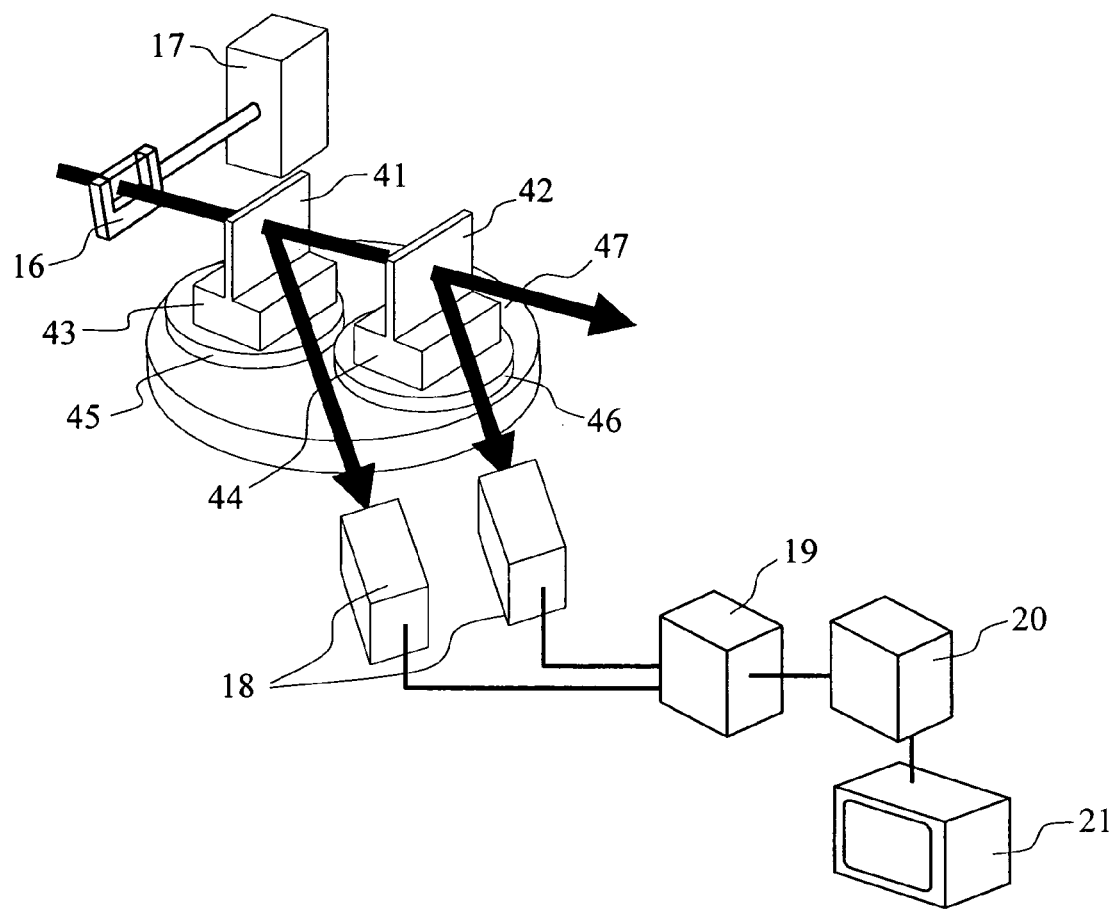
FIG. 19 is a view showing a configuration example of the X-ray imaging system according to the present invention.

As shown in FIG. 19, crystal wafers 41 and 42 are formed on separate crystal blocks 43 and 44, respectively. The crystal blocks are mounted on rotational mechanisms 45 and 46, respectively, and further, the rotational mechanisms are mounted on one crystal block positioning mechanism 47. The crystal wafers are adjusted to have the same angular difference as that of the first and second embodiments by use of the rotational mechanisms 45 and 56. In this instance, the angular difference must be controlled with high accuracy, and thus, a small-size horizontal rotating table using a tangential bar may be used. Also, in order to reduce drift or the like, a measuring mechanism using a laser or a high-accuracy encoder can be used to control rotation so that the measured value thereof is fixed. A precise positioning table using a tangential bar can be used as the crystal block positioning mechanism 47, as in the case of the first and second embodiments. Incidentally, a table having a thicker rotation shaft and a higher load resistance, as compared to that used in the first and second embodiments, is suitable in order to mount the rotational mechanisms 45 and 56 and the single crystal blocks 43 and 44 with high stability.

The measurement is performed in the same manner as the first embodiment, each obtained image is used for calculation of the spatial distribution image of the refraction angle and phase-map, and each projection image or sectional image is displayed on the display unit 21 under an operator command or the like. Also, the sample holder 16 and the sample holder positioning mechanism 17 may be replaced by the same as those used in the fourth embodiment to obtain the sectional image of the sample by the method of the fourth embodiment.

As described above, even if the sample is of large size, the fifth embodiment enables detecting the projection image and the sectional image using as the contrast the refraction angle and the phase caused by the sample, and thus enables nondestructive observation of the internal structure of the sample with high sensitivity, in a short measurement time, with low X-ray damage, and without consideration of fluctuations in the incident X-ray intensity or the like.

Sixth Embodiment

Figure 20:
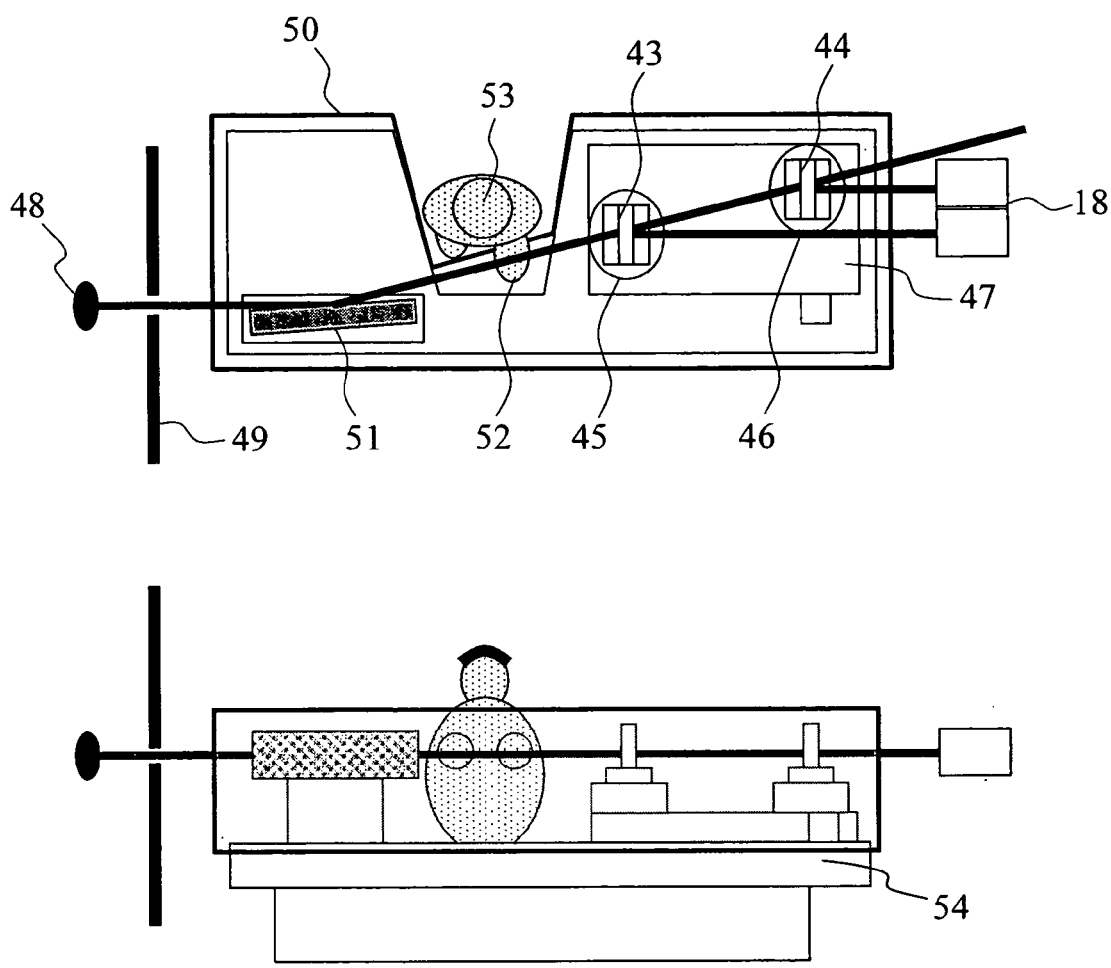
FIG. 20 is a view showing a configuration example of the X-ray imaging system according to the present invention.

FIG. 20 shows an embodiment of a mammography system (or a breast cancer diagnosis system) as an example of a diagnosis system that exploits the feature of the present invention, that is, the advantage of "being highly sensitive particularly to light elements and thus being suitable for observation of biological soft tissues consisting mainly of the light elements." The diagnosis system requires an X-ray source, a means for minimizing X-ray dosage due to X-ray irradiation, a large field of view that allows obtaining an object at a time, and high stability that allows obtaining the same image even if measurement is performed many times. Thus, the sixth embodiment is provided with an X-ray source 48, a means for preventing X-ray irradiation of a region other than an irradiation region of the object, such as an X-ray shield wall 49 and an X-ray shield cover 50, and an asymmetric crystal plate 51 for enlarging an X-ray beam, in addition to the basic configuration of the fourth embodiment.

The X-ray shield wall 49 which is disposed between the X-ray source 48 and the asymmetric crystal plate for enlargement 51, and which serves to shield unnecessary X-rays of X-rays emitted from the X-ray source 48, is made of a thick wall containing lead or the like, and can shield 100% of the X-ray intensity. The X-ray shield cover 50 serves to cover the overall main constituent part of the system, including the asymmetric crystal plate for enlargement 51, the crystal wafers, and so on, and prevents irradiation of an object 52 or the X-ray imager 18 with scattered X-rays produced by the crystals. Since the intensity of the scattered X-rays is not very strong, an acrylic sheet containing lead, an iron sheet laminated with thin lead, or the like is used for this shield cover. A part for placement of the object 52 within the X-ray beam is provided with a concave portion as shown in FIG. 20, and a part of the object 52, other than a part to be irradiated with beams, is set not to be irradiated with the X-rays.

Strain generated between the asymmetric crystal plate for enlargement 51 and the diffraction plane interval of the crystal wafer 41 caused by heat generation of a subject 53, or the like is reduced by making a distance of 30 cm or more between the subject 53 and the asymmetric crystal plate for enlargement 51 and between the subject 53 and the crystal wafer 41. Also, the influence of floor vibration or the like caused by replacement of the subject 53 is reduced by mounting, on the same antivibration mount 54, the asymmetric crystal plate for enlargement 51 and the single crystal blocks 43 and 44 which mount thereon the crystal wafers 41 and 42, respectively. The antivibration mount 54 is also of concave configuration in the vicinity of the subject 53, and has a structure such that the subject does not come into contact with the antivibration mount.

In breast cancer diagnosis, the thickness of the object (or the breast) varies greatly among individuals. Thus, the thicknesses of individual objects are premeasured, and the optimum energy of X-rays and a diffraction plane to be used are determined in advance. The measurement is performed following a flowchart of FIG. 13, as described with reference to the first embodiment.

EXPLANATION OF REFERENCE NUMERALS

1: beam splitter, 2: mirror, 3: analyzer, 4: incident X-ray, 5: beam, 6: beam, 7: interference beam, 8: interference beam, 9: sample, 10: single crystal made of flat sheet, 11: crystal wafer, 12: crystal wafer, 13: single crystal block, 14: rotational mechanism, 15: crystal block positioning mechanism, 16: sample holder, 17: sample holder positioning mechanism, 18: X-ray imager, 19: controller, 20: processing unit, 21: display device, 22: X-ray, 23: diffracted X-ray, 24: transmitted X-ray, 25: diffracted X-ray, 26: transmitted X-ray, 27: crystal wafer, 28: crystal wafer, 29: single crystal block, 30: X-ray, 31: diffracted X-ray, 32: transmitted X-ray, 33: diffracted X-ray, 34: transmitted X-ray, 35: rotational mechanism, 36: single crystal block, 37: rotational mechanism, 38: sample holder, 39: sample rotating mechanism, 40: sample cell, 41: crystal wafer, 42: crystal wafer, 43: crystal block, 44: crystal block, 45: rotational mechanism, 46: rotational mechanism, 47: crystal block positioning mechanism, 48: X-ray source, 49: X-ray shield wall, 50: X-ray shield cover, 51: asymmetric crystal plate for enlargement, 52: object, 53: subject, 54: antivibration mount, 55: sample, 56: measuring mechanism, 58: piezo

What is claimed is:

1. An X-ray imaging system, comprising:
    a means for irradiating a sample with an X-ray beam;
    a plurality of analyzer crystals arranged in series on an optical path of the X-ray beam, and configured to split the X-ray beam that has passed through the sample into a plurality of reflected X-ray beams and transmitted X-ray beams;
    a rotational mechanism that adjusts an angle between the plurality of analyzer crystals;
    a plurality of X-ray imagers that detect the plurality of reflected X-ray beams; and
    a processing unit that performs operations on outputs from the plurality of X-ray imagers to thereby obtain an image using as contrast refraction angles and phase-shifts of the X-ray beams caused by the sample;
    wherein said processing unit measures said refraction angles from said outputs from the plurality of X-ray imagers.

2. The X-ray imaging system according to claim 1, comprising:
    a mechanism for rotating the sample with respect to the optical path of the X-ray beam; and
    a means for reconstructing a sectional image of the sample from a plurality of sample images obtained by irradiation of the X-ray beams from a plurality of different directions.

3. The X-ray imaging system according to claim 1, wherein the plurality of analyzer crystals are held on one rotating table capable of rotating at a minute angle with respect to the optical path of the X-ray beam.

4. The X-ray imaging system according to claim 1, wherein the plurality of analyzer crystals are a plurality of thin crystal wafers formed on one single crystal block.

5. The X-ray imaging system according to claim 1, wherein diffraction lattice planes of the plurality of analyzer crystals are substantially perpendicular to the respective crystal surfaces.

6. The X-ray imaging system according to claim 1, wherein the diffraction lattice planes of the plurality of analyzer crystals are substantially parallel to the respective crystal surfaces.

7. The X-ray imaging system according to claim 1, wherein the diffraction lattice planes of the plurality of analyzer crystals are nonparallel to the respective crystal surfaces.

8. The X-ray imaging system according to claim 4, wherein the single crystal block has a notch extending from the lateral side between two adjacent analyzer crystals, and the rotational mechanism has a piezo that adjusts an interval of an open end of the notch.

9. The X-ray imaging system according to claim 1, wherein the plurality of analyzer crystals are thin crystal wafers formed respectively on separate crystal blocks, and the crystal blocks are disposed on a positioning mechanism capable of adjusting a relative angle.

10. An X-ray imaging method, comprising the steps of:
    irradiating a sample with an X-ray beam;
    entering in sequence the X-ray beam that has passed through the sample into a plurality of analyzer crystals having diffraction lattice planes of different angles, thereby splitting the X-ray beam into a plurality of reflected X-ray beams and transmitted X-ray beams;
    detecting the reflected X-ray beams by a plurality of X-ray imagers; and performing operations to thereby obtain from a plurality of detected images a sample image using as contrast refraction angles and phase-shifts of the X-ray beams caused by the sample;

wherein said processing unit measures said refraction angles from said outputs from the plurality of X-ray imagers.

11. The X-ray imaging method according to claim 10, wherein the sample is rotated with respect to the optical path of the X-ray beam, and a sectional image of the sample is reconstructed from a plurality of sample images obtained by irradiation of the X-ray beams from a plurality of different directions.

12. The X-ray imaging method according to claim 10, wherein the plurality of analyzer crystals are rotated at a time at a minute angle with respect to the optical path of the X-ray beam, and the sectional image of the sample is reconstructed from a plurality of sample images obtained at a plurality of different angles.

13. The X-ray imaging method according to claim 10, wherein the plurality of analyzer crystals are rotated relative to the optical path of the X-ray beam to thereby obtain a plurality of sample images, and an image using as contrast any one of refraction angles and phase-shifts of the X-ray beams caused by the sample is obtained from the plurality of obtained sample images, by performing operations.

14. The X-ray imaging method according to claim 10, wherein X-ray diffractions by the analyzer crystals are used to detect a refraction angle, caused by the sample, of the X-ray beam.

15. An X-ray imaging system, comprising:

a means for irradiating a sample with an X-ray beam;

a plurality of analyzer crystals arranged in series on an optical path of the X-ray beam, and configured to split the X-ray beam that has passed through the sample into a plurality of refracted X-ray beams and transmitted X-ray beams;

a rotational mechanism that adjusts an angle between the sample and the plurality of analyzer crystals;

a plurality of X-ray imagers that detect the plurality of refracted X-ray beams; and a processing unit that performs operations on outputs from the plurality of X-ray imagers to thereby obtain an image, using refraction angles and phase-shifts of the X-ray beams caused by the sample as contrast;

wherein said processing unit measures said refraction angles from said outputs from the plurality of X-ray imagers.

16. The X-ray imaging apparatus according to claim 15, wherein the analyzer crystals are configured to create X-ray diffractions used by the processing unit to detect a refraction angle of the X-ray beam caused by the sample.

17. The X-ray imaging apparatus according to claim 16, wherein an analyzer crystal is configured to diffract an X-ray only when the incident angle of the X-ray is in the vicinity of a Bragg angle.

18. The X-ray imaging apparatus according to claim 17, wherein an analyzer crystal is configured such that when the incident angle of the X-ray deviates from the vicinity of the Bragg angle, refraction changes drastically such that the X-ray is transmitted.

19. The X-ray imaging method according to claim 14, wherein an X-ray is diffracted by an analyzer crystal only when the incident angle of the X-ray is in the vicinity of a Bragg angle.

20. The X-ray imaging method according to claim 19, wherein when the incident angle of the X-ray deviates from the vicinity of the Bragg angle, refraction changes drastically such that the X-ray is transmitted.

* * * * *